US007612081B2

(12) United States Patent
Giannini et al.

(10) Patent No.: US 7,612,081 B2
(45) Date of Patent: Nov. 3, 2009

(54) 7-POLYAMINOALKYL(OXY) IMINOMETHYLCAMPTOTHECINS BEARING PROTECTIVE GROUPS

(75) Inventors: Giuseppe Giannini, Pomezia (IT); Claudio Pisano, Aprilla (IT); Loredana Vesci, Rome (IT); Maria Ornella Tinti, Rome (IT); Lucio Merlini, Milan (IT); Sergio Penco, Milan (IT); Franco Zunino, Milan (IT)

(73) Assignees: Istituto Nazionale per lo Studio e la Cura dei Tumori, Milan (IT); Sigma Tau Industrie Farvaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/564,637

(22) PCT Filed: Jul. 6, 2004

(86) PCT No.: PCT/IT2004/000374
§ 371 (c)(1),
(2), (4) Date: Aug. 10, 2006

(87) PCT Pub. No.: WO2005/005431

PCT Pub. Date: Jan. 20, 2005

(65) Prior Publication Data
US 2007/0043067 A1     Feb. 22, 2007

(30) Foreign Application Priority Data
Jul. 14, 2003  (IT) .......................... RM2003A0344

(51) Int. Cl.
*A61K 31/4745* (2006.01)
*C07D 491/22* (2006.01)
(52) U.S. Cl. ......................... 514/283; 546/48; 435/184
(58) Field of Classification Search ................ 514/283; 546/48; 435/184
See application file for complete search history.

(56) References Cited
U.S. PATENT DOCUMENTS

| | | | |
|---|---|---|---|
| 6,242,457 B1 * | 6/2001 | Penco et al. ............... 514/283 |
| 6,589,939 B2 * | 7/2003 | Penco et al. ............... 514/25 |
| 7,105,492 B2 * | 9/2006 | Dallavalle et al. ........... 514/25 |
| 2001/0008939 A1 | 7/2001 | Penco et al. | |

FOREIGN PATENT DOCUMENTS

| | | |
|---|---|---|
| EP | 1 044 977 | 10/2000 |
| WO | 97/00876 | 1/1997 |
| WO | 03/101995 | 12/2003 |
| WO | 2004/083214 | 9/2004 |

OTHER PUBLICATIONS

International Search Report for PCT/IT2004/000374 dated Dec. 21, 2004.

Dallavalle et al., *Novel Cytotoxic 7-Iminomethyl and 7-Aminomethyl Derivatives of Camptothecin*, Bioorg. Med. Chem. Lett., vol. 11, 2001, pp. 291-294, XP002286415.
Dallavalle et al., *Perspectives in camptothecin development*, Expert. Opin. Ther. Patents, vol. 12, No. 6, 2002, pp. 837-844, XP002251117.
Dallavalle et al., *Novel 7-Oxyiminomethyl Derivatives of Camptothecin with Potent in Vitro and in Vivo Antitumor Activity*, J. Med. Chem., vol. 44, No. 20, May 9, 2001, pp. 3264-3274, XP002307863.
Horwitz et al, "Antiviral Action of Camptothecin", Antimicrobial Agents and Chemotherapy, Nov. 1972, pp. 395-401.
Li et al, "Three Inhibitors of Type 1 Human Immunodeficiency Virus Long Terminal . . . ", Proc. Natl. Acad. Sci. USA, vol. 99, pp. 1839-1842, Mar. 1993.
Garcia-Carbonero et al, "Current Perspectives on the Clinical Experience, Pharmacology . . . ", Clinical Cancer Research, vol. 8, 641-661, Mar. 2002.
Dallavalle et al, "Perspectives in Camptothecin Development", Expert Opinion Ther. Patents (2002) 12(6) 837; XP-002251117.
Lesueur-Ginot et al, "Homocamptothecin, an E-Ring Modified Camptothecin . . . ", Cancer Research 59, 2939-2943, Jun. 15, 1999.
Vladu et al, "7- and 10-Substituted Camptothecins: Dependence of Topoisomerase . . . ", Molecular Pharmacology, 57:243-251 (2000).
Dallavalle et al, "Novel 7-Oxyiminomethyl Derivatives . . . ", J. Med. Chem. 2001, 44, 3264-3274.
Kantarjian et al, "Phase I Study of Topotecan, A New Topoisomerase . . . ", Blood, vol. 81, No. 5 (Mar. 1, 1993), pp. 1146-1151.
Kaufmann et al, "Topoisomerase II Levels and Drug Sensitivity . . . ", Blood, vol. 83, No. 2 (Jan. 15, 1994): pp. 517-530.

(Continued)

*Primary Examiner*—Charanjit S Aulakh
(74) *Attorney, Agent, or Firm*—Lucas & Mercanti, LLP

(57) ABSTRACT

Compounds are disclosed with the general formula

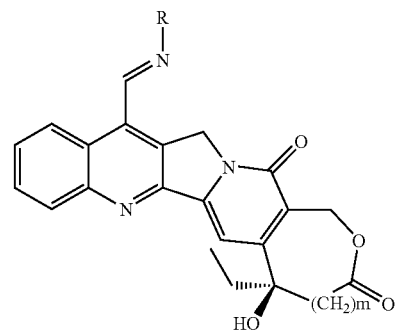

in which the groups are as defined in the description here below and characterized by the presence of polyamine substituents on the imine/oxime residue, such amine groups being in turn protected by suitable protective groups. Said compounds are endowed with potent topoisomerase I inhibiting activity and therefore are useful as medicaments for the treatment of tumors and viral and parasite infections.

9 Claims, No Drawings

OTHER PUBLICATIONS

Lichtman et al, "Chemotherapy in the Elderly . . . ", Cancer Control, Nov./Dec. 2000, vol. 7, No. 6., pp. 548-556.

Bodley et al, "Molecular and Cytotoxic Effects . . . ", Proc. Natl. Acad. Sci. USA, vol. 92, pp. 3726-3730, Apr. 1995.

Priel et al, "The Topoisomerase I Inhibitor . . . ", Journal of Virology, Aug. 1991, p. 4137-4141.

Lavergne et al, "Homocamptothecins: Synthesis and Antitumor Activity . . . ", J. Med. Chem. 1998, 41, 5410-5419.

* cited by examiner

7-POLYAMINOALKYL(OXY) IMINOMETHYLCAMPTOTHECINS BEARING PROTECTIVE GROUPS

This application is the US national phase of international application PCT/IT2004/000374 filed 6 Jul. 2004 which designated the U.S. and claims benefit of IT RM 2003 A 000344 filed 14 Jul. 2003, the entire contents of each of which are hereby incorporated by reference.

The invention disclosed herein relates to compounds useful as medicaments, and particularly to camptothecin derivatives with substituents in position C-7, containing polyamine residues in which the amine residues are protected with protective groups such as Boc, to processes for their preparation, to their use as active agents with topoisomerase I inhibiting activity and to pharmaceutical compositions containing them as active ingredients.

BACKGROUND TO THE INVENTION

Camptothecin is an alkaloid isolated by Wall et al. [*J. Am. Chem. Soc.*, 1966, 88, 3888-3890] for the first time from the tree *Carmptotheca acumiiata*, native to China and belonging to the Nyssaceae family.

The molecule consists of a pentacyclic structure with a lactone in ring E, which is essential for cytotoxicity.

For a review of the camptothecins and the problems relating to their use as medicaments as well as the solving of such problems, the reader is referred to EP 1 044 977, filed in the name of the present applicants.

The polyamines have for some time now been the subject of great interest in medicinal chemistry.

Putrescine, spermidine and spermine are the most intensively studied polyamines, in that they occur naturally in both prokaryotic and eukaryotic cells. Their role in cell physiology would appear to be multiple and, in certain respects, still unknown [*J. Med. Chem.*, 2001, 44, 1-26]. At physiological pH these compounds are present as polycations, are capable of interacting with a substantial variety of cell constituents, such as RNA, DNA, nucleotides, proteins and other biological substances of an acid nature [*J. Cell Biochem.*, 1991, 46, 37-47].

In oncology the polyamines are the subject of study for a number of reasons, namely, their polycationic nature at physiological pH, their influence on the ion channels of the cell membranes, and their interaction with various important transcriptional factors in human tumour forms [*Biochemistry* 1999, 38, 14765-74].

The conjugation of polyamines with cytotoxic drugs has also been described, for example with chlorambucil [*Cancer Res.*, 1992, 52, 4190-5], where a substantial improvement in the therapeutic index has been observed, but also as a form of chemoprevention in combination with 3-indolylcarbinol [*BMC-Cancer* 2003, 3:2, 1471-2407].

Less frequent is the study of polyamine derivatives in protected form: for example, N-benzyl-derivatives [*J. Med. Chem.*, 2001, 44, 3653-64].

The polyamines can be bound to cytotoxic molecules in order to influence their cell transport: for example, spermines have been conjugated with acridines [*J. Med. Chem.*, 2002, 45, 5098-111] for the purposes of favouring a selective release of the latter at tumour cell level.

Polyamine residues have also been inserted in camptothecins (CPT) in position 7, such as iminomethyl derivatives [*Bioorganic & Medicinal Chemistry Letters*, 2001, 11, 291-4], and, in particular, the compound derived from spermine has been described in international patent application WO 0053607 filed in the name of the present applicant.

SUMMARY OF THE INVENTION

It has now been surprisingly found that camptothecins substituted in position 7 by means of an iminomethyl or oxyiminomethyl bond, where the imine and oxime groups derive from amines or hydroxylamines containing polyaminoalkyl residues (e.g. spermine, spermidine, putrescine), when present in protected form, display substantial anticancer activity, distinctly superior to that of the same derivatives in unprotected form.

This anticancer potency is comparable to that of compounds currently used in oncological clinical practice, and therefore the derivatives which are the subject of the present invention may make a major contribution to enriching the armamentarium available for the fight against cancer.

The compounds which are the subject of the present invention have the following general formula (I):

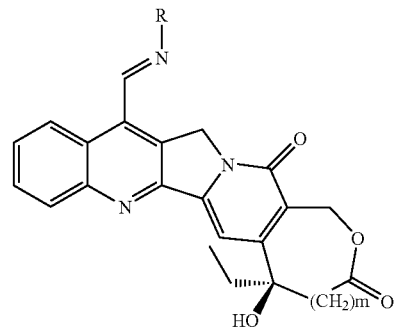

in which

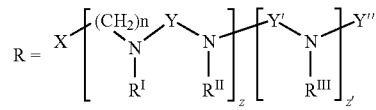

m is the number 0 or 1;

Z and Z', which can be the same or different, are an integer ranging from 0 to 2;

Y and Y', which can be the same or different, are $(CH_2)n_1$; $(CH_2)n_2$-$CH[NR^{VII}(CH_2)n_4$-$NHR^1]$—$(CH_2)n_3$; $CH_2$—$CH[CH_2$—$CH_2]_2$— or $(CH_2)n_2N[(CH_2)n_4$—$NHR^{IV}]$—$(CH_2)n_3$;

Y" is selected from the group consisting of H; cycloalkyl $C_3$-$C_7$; $(CH_2)n_5$-$N[CH_2$—$CH_2]_2N$—$(CH_2)n_6NHR^V$; $(CH_2)n_7$-$CH[CH_2$—$CH_2]_2NR^V$;

X is O, or is a simple bond;

$n$-$n_8$, which can be the same or different, are an integer ranging from 0 to 5;

$R^I$, $R^{II}$, $R^{III}$, $R^{IV}$, and $R^V$, which can be the same or different, are a protective group for the nitrogen to which they are bound; $CO_2R^{VI}$; $CO_2CH_2Ar$; $CO_2$(9-fluorenylmethyl); $(CH_2)n_5$-$NHCO_2R^{VI}$; $CH_2Ar$; $COAr$; $(CH_2)n_5$-$NHCO_2CH_2Ar$; $(CH_2)n_5$-$NHCO_2$-(9-fluorenylmethyl).

$R^{VI}$ is a straight or branched ($C_1$-$C_6$) alkyl;

$R^{VII}$ is H or $R^I$-$R^V$;

Ar is a $C_6$-$C_{12}$ aromatic residue, such as phenyl, optionally substituted with one or more groups selected from: halogen, hydroxy, $C_1$-$C_5$ alkyl, $C_1$-$C_5$ alkoxy, phenyl, cyano, nitro, —$NR^{VIII}R^{IX}$, where $R^{VIII}$ and $R^{IX}$, which can be the same or different, are hydrogen, straight or branched ($C_1$-$C_5$) alkyl, or Ar is a heterocyclic group, said heterocyclic group containing at least one heteroatom selected from a nitrogen atom, optionally substituted with a ($C_1$-$C_5$) alkyl group, and/or oxygen and/or sulphur; said heterocycle can be substituted with one or more groups selected from halogen, hydroxy, $C_1$-$C_5$ alkyl, $C_1$-$C_5$ alkoxy, phenyl, cyano, nitro, —$NR^{VIII}R^{IX}$, where $R^{VIII}$ and $R^{IX}$, which can be the same or different, are hydrogen, straight or branched ($C_1$-$C_5$) alkyl, the $N_1$-oxides, racemic mixtures, their individual enantiomers, their individual diastereoisomers, the E and Z forms, their mixtures, and pharmaceutically acceptable salts.

The present invention comprises the use of compounds with the above-mentioned general formula (I) as active ingredients for medicaments, particularly for medicaments useful as topoisomerase I inhibitors. Among the therapeutic applications deriving from the topoisomerase inhibiting activity we should mention tumours and viral and parasite infections.

The present invention comprises pharmaceutical compositions containing formula (I) compounds as active ingredients, in admixture with pharmaceutically acceptable vehicles and excipients.

DETAILED DESCRIPTION OF THE INVENTION

What is meant by a protective group, as referring to the various $R^I$, $R^{II}$, $R^{III}$, $R^{IV}$, and $R^V$, is a group that favours the capture of the molecule by the cell. Whereas the present invention is based on the discovery that protective groups on the amine nitrogens confer potent anticancer activity upon the molecules, and since the inventors do not wish to be tied to any particular theoretical consideration, it is believed that the protective groups should be bulky groups of a lipophilic nature. Preferred examples of protective groups are: $CO_2R^{VI}$; $CO_2CH_2Ar$; $CO_2$-(9-fluorenylmethyl); $(CH_2)n_5$-$NHCO_2R^{VI}$; $(CH_2)n_5NHCO_2$—$CH_2Ar$; $CH_2Ar$; $COAr$; $(CH_2)n_5$-$NHCO_2$-(9-fluorenylmethyl), in which the variable groups are defined as above.

A first group of particularly preferred compounds comprises formula (I) compounds with a 6-term lactone ring (m=0) and, among these, particularly:
  tert-butylester of 20S-(4-{[3-(7-camptothecinylidene-amino)-propyl]-tert-butoxycarbonyl-amino}-butyl)-(3-tert-butoxycarbonyl-aminopropyl)-carbamic acid;
  tert-butylester of 20S-(4-{[3-(7-camptothecinylidene-amino)-propyl]-tert-butoxycarbonyl-amino}-butyl)-carbamic acid;
  tert-butylester of 20S-[3-(7-camptothecinylidene-amino)-butyl]-carbamic acid;
  20S-7-[3-(T-tert-butoxycarbonylamino)propoxyimino-methyl]-camptothecin.

A second group of preferred compounds comprises formula (I) compounds with a 7-term lactone ring, the synthesis of which is described in [*J. Med. Chem.* 1993, 41, 5410], and, among these, particularly:
  tert-butylester of 20RS-(4-{[3-(7-homocamptotheci-nylidene-amino)-propyl]-tert-butoxycarbonyl-amino}-butyl)-(3-tert-butoxycarbonylaminopropyl)-carbamic acid;
  tert-butylester of 20RS-(4-{[3-(7-homocamptotheci-nylidene-amino)-propyl]-tert-butoxycarbonyl-amino}-butyl)-carbamic acid;
  tert-butylester of 20RS-[3-(7-homocamptothecinylidene-amino)-butyl]-carbamic acid;
  20R,S-7-[3-(N-tertbutoxycarbonylamino)propoxyimino-methyl]-homocamptothecin.

The compounds disclosed in the present invention are topoisomerase I inhibitors and are therefore useful as medicaments, particularly for the treatment of diseases that benefit from inhibition of said topoisomerase. In particular, the compounds according to the present invention display antiproliferative activity, and are therefore used for their therapeutic activity, and possess physicochemical properties which make them suitable for formulation in pharmaceutical compositions.

The pharmaceutical compositions contain at least one formula (I) compound as the active ingredient, in an amount such as to produce a significant therapeutic effect. The compositions covered by the present invention are entirely conventional and are obtained by using methods which are common practice in the pharmaceutical industry. According to the administration routes opted for, the compositions will be in solid or liquid form, suitable for oral, parenteral or intravenous administration. The compositions according to the present invention contain, along with the active ingredient, at least one pharmaceutically acceptable vehicle or excipient. These may be particularly useful coadjuvants, for example, solubilising agents, dispersion agents, suspension agents, or emulsifying agents.

Formula (I) compounds can also be used in combination with other active ingredients, for example, anticancer drugs or other drugs with antiparasite or antiviral activity, both in separate forms and in single-dosage forms.

The compounds according to the present invention are useful as medicaments with anticancer activity, for example in lung cancers such as non-microcytoma lung cancer, or in colorectal and prostate cancer and glioma.

The following examples further illustrate the invention.

Preparation 1

7-Formyl-camptothecin

To a solution of 2.0 g (4.73 mmol) of 7-dimethylacetal-camptothecin in 18 mL of $CH_2Cl_2$, cooled to 0° C., were added 12 mL of TFA and a few drops of H2O. After one night at room temperature the reaction is complete with the formation of a product with Rf=0.42 ($CH_2Cl_2$/MeOH 92:8). The reaction mixture was purified by chromatography on $SiO_2$ with $CH_2Cl_2$/MeOH (from 98:2 to 92:8) to give 1.4 g (3.72 mmol; yield 79%) of the expected product as a yellow solid.

Preparation 2

N',N'',N'''-triBoc-spermine
  N',N'',N'''-triBoc-spermine was prepared according to the process described in the literature [*Tetrahedron Letters* 1998, 39, 439-42].

Preparation 3

N',N''-diBoc-spermidine
  The compound was prepared with a process equivalent to that disclosed for spermine.

Preparation 4

N'-Boc-putrescine
  This compound is commercially available

EXAMPLE 1

7-[(N',N'',N'''-tert-butoxycarbonyl)-spermine-iminomethyl]-20S-camptothecin [ST2544].

272 mg (0.72 mmol) of 7-formylcamptothecin were dissolved in 20 mL of anhydrous $CH_2Cl_2$ in a 100 mL flamed flask. 44 mg of $Yb(OTf)_3$ (0.07 mmol; 0.1 eq.) were added to the solution and then 700 mg (1.4 mmol; 2 eq.) of tri-Boc-spermine dissolved in 12 mL of anhydrous $CH_2Cl_2$ and molecular sieves, keeping the reaction flask sheltered from the light. After 16 h at room temperature 1.9 g (4.2 mmol; 3 eq. in relation to spermine) of a resin functionalized with isocyanate groups (loading 2.2 mmol/g) were added as a scavenger of the excess amine.

The reaction mixture was left for another 16 h at room temperature before being filtered on celite to remove the molecular sieves and the scavenger resin; the solvent was removed in vacuo and the crude reaction product was purified by preparative HPLC chromatography ($CH_3CN/MeOH=90$:10; 8 mL/min; RP-18, 250×25 mm, 7 μm) to give 500 mg (0.58 mmol; yield 81%) of product as a yellow solid.

MS(IS):$[MH]^+=860.8$ $[M-1]^-=858.7$ $^1H$ NMR (300 MHz, $CDCl_3$, δ): 1.0-1.1 (t, 3H, $CH_3$), 1.4-2.0 (m, 35H, 3×tBu+4×$CH_2$), 2.0-2.1 (q, 2H, $CH_2$), 3.0-3.3 (m, 10H, 5×$CH_2$), 3.85-3.95 (m, 2H, $CH_2$), 5.3-5.4 (d, 1H, CH), 2.55 (s, 2H, $CH_2$), 5.75-5.85 (d, 1H, CH), 7.7-7.9 (m, 3H, 3×CH), 8.25-8.35 (d, 1H, CH), 8.45-8.55 (d, 1H, CH), 9.4 (s, 1H, CH). $^{13}CNMR$ (75.4 MHz, $CDCl_3$, δ): 8.0; 28.6; 28.7; 31.8; 47.0; 52.7; 66.6; 72.9; 79.5; 97.8; 118.9; 126.2; 127.6; 128.5; 139.3; 130.8; 146.2; 149.9; 150.0; 152.9; 155.7; 157.6; 174.0.

EXAMPLE 2

7-[(N', N''-tert-butoxycarbonyl)-spermidine-iminomethyl]-20S-camptothecin [ST2598].

Using the same process disclosed in Example 1, the title product was obtained.

Yield=22% MS(IS): $[MH]^+=704.6$ $[M+Na]^+=726.6$ $^1H$ NMR (300 MHz, $CDCl_3$, δ): 1.0-1.1 (t, 3H, $CH_3$), 1.4-2.1 (m, 26H, 2×tBu+4×$CH_2$), 3.0-3.4 (m, 4H, 2×$CH_2$), 3.75-3.95 (m, 4H, 2×$CH_2$), 5.25-5.35 (d, 1H, CH), 5.55 (s, 2H, $CH_2$), 5.75-5.85 (d, 1H, CH), 7.7-7.9 (m, 3H, 3×CH), 8.25-8.35 (d, 1H, CH), 8.45-8.55 (d, 1H, CH), 9.4 (s, 1H, CH). $^{13}CNMR$ (75.4 MHz, $CDCl_3$, δ): 8.0; 28.6; 28.7; 32.1; 47.4; 51.7; 52.9; 53.6; 66.7; 69.7; 72.9; 79.7; 98.0; 98.4; 119.0; 122.5; 123.1; 126.4; 127.7; 128.6; 130.2; 130.4; 131.0; 131.3; 146.4; 150.1; 153.1; 156.0; 156.4; 157.9; 174.2.

EXAMPLE 3

7-[3-(N-tert-butoxycarbonyl)-amino-1-propoxyiminomethyl]20S-camptothecin (ST2664)

To a suspension of -7-(3-aminopropoxyiminomethyl)-20S-camptothecin (20 mg, 0.045 mmol) in 5 ml of anhydrous THF are added 10 mg of $(Boc)_2O$ (1 equivalent) and 7 μl of $Et_3N$ (1 equivalent); the mixture is left to react at room temperature for 30 h, at the end of which period the reaction is almost complete. The reaction is monitored by TLC, eluting with $CH_2Cl_2:CH_3OH=9:1$.

The THF is evaporated and the solid extracted with $CH_2Cl_2$; the organic phase is washed with water (twice) and with brine (once). The solution is anhydrified with $Na_2SO_4$, filtered and brought to dryness. 16 mg of product consisting of a mixture of E and Z isomers is obtained (yield: 64%).

Rf: 0.38 in $CH_2Cl_2:CH_3OH=98:2$. M.p.: 141-142° C. $^1H$-NMR (300 MHz, DMSO-d6, δ): 0.87 (t, $H_3$-18E+$H_3$-18Z), 1.37 (s, $H_9$ t-butyl E), 1.30 (s, $H_9$ t-butyl Z), 1.67 (m, $H_2$-19Z+—$CH_2CH_2CH_2$-Z), 1.87 (m, $H_2$-19E+—$CH_2CH_2CH_2$-E), 2-83 (t, $CH_2$—N-Z), 3.07 (t, $CH_2$—N-E), 4.12 (t, $CH_2$—O-Z), 4.35 (t, $CH_2$—O-E), 5.17 (s, H-17-Z), 5.32 (s, H-17-E), 5.40 (s, H-5-E), 6.50 (s, OH-E+OH-Z), 6.75 (t, NH-Z), 6.90 (t, NH-E), 7.25 (s, H-14-Z), 7.32 (s, H-14-E), 7.75 (m, H-11-E+H-11-Z), 7.90 (m, H-10-E+H-10-Z), 8.02 (d, H-12-Z), 8.20 (d, H-12-E+H-9-Z), 8.40 (s, —CH=N-Z), 8.6 (d, H-9-E), 9.32 (s, —CH=N-E). E:Z ratio=88:22 (by NMR).

EXAMPLE 4

7-[N-(N'-tert-butoxcarbonyl)-putrescinimino-methyl]-20S-camptothecin [ST26151]

Using the same synthesis process disclosed in Example 1, the title product was obtained.

Yield=78% MS(IS):$[MH]^+=547.7$ $^1H$ NMR (300 MHz, $CDCl_3$, δ): 1.0-1.1 (t, 3H, $CH_3$), 1.45 (s, 9H, tBu), 1.65-2.0 (m, 4H, 2×$CH_2$), 3.2-3.35 (q, 2H, $CH_2$), 3.9-4.0 (t, 2H, $CH_2$), 5.3-5.4 (d, 1H, CH), 5.55 (s, 2H, $CH_2$), 5.75-5.85 (d, 1H, CH), 7.7-7.9 (m, 3H, 3×CH), 8.25-8.35 (d, 1H, CH), 8.45-8.55 (d, 1H, CH), 9.4 (s, 1H, CH).

EXAMPLE 5

7-[4-(N-tert-butoxycarbonyl)-piperidinyl-methyliminomethyl-20S-camiptothecin [ST2665)

To a suspension of 7-formylcamptothecin (60 mg, 0.159 mmol) in 5 ml of $CH_2Cl_2$ (distilled on $CaCl_2$ and conserved on sieves) are added 119 mg (0.477 mmol, 3 eq.) of 1-Boc-4-aminomethylpiperidine hydrochloride, 40 μl of pyridine and 6 mg of $Yb(OTf)_3$ (10% by weight in relation to the aldehyde) and the mixture is left to react at room temperature for 5 days (TLC: $CH_2Cl_2:CH_3OH=98:2$).

The product is purified by flash chromatography (eluent: $CH_2Cl_2:CH_3OH=99:1$). Yellow solid. Yield: 20%. M.p. 200° C. dec. Rf of the reaction product: 0.37 in $CH_2Cl_2$:$CH_3OH=96:4$.

$^1H$-NMR (300 MHz, DMSO-$d_6$; δ): 0.87 (t, $CH_2CH_3$), 1.32 (s, t-butyl), 1.67-2.00 (m, $CH_2CH_3$+2—$CH_2$pip.+—CH pip.), 2.55-2.85 (m, —$CH_2$-pip.), 3.80 (m, —$CH_2$—N), 3.97 (m, —$CH_2$-pip.), 5.35 (s, H-17), 5.42 (s, H-5), 6.50 (s, OH), 7.35 (s, H-14), 7-70-7.80 (m, H-11), 7.85-7.95 (m, H-10), 8.20 (dd, H-12), 8.72 (dd, H-9), 9.42 (s, —CH=N).

EXAMPLE 6

7-[(N',N''-Di-benzyloxycarbonyl)-spermidineiminomethyl]-20S-camptothecin [ST2729].

Using the same synthesis process disclosed in Example 1, the title product was obtained.

Yield=35% MS(IS): $[MH]^+=772.9$ $[M+Na]^+=794.9$ $^1H$ NMR (300 MHz, $CDCl_3$, δ): 1.0-1.1 (t, 3H, $CH_3$), 1.4-2.1 (m, 8H, 4×$CH_2$), 3.2-3.6 (m, 6H, 3×$CH_2$), 3.95 (s, 2H, $CH_2$), 5.1-5.2 (d, 4H, 2×$CH_2$), 5.4-5.9 (m, 4H, 2×$CH_2$), 7.2-7.45 (m, 10H, 10×CH), 7.7-7.9 (m, 3H, 3×CH), 8.25-8.5 (m, 2H, 2×CH), 9.4 (s, 1H, CH). $^{13}CNMR$ (75.4 MHz, $CDCl_3$, δ): 8.0; 27.2; 31.7; 41.0; 52.8; 66.5; 66.6; 67.2; 72.9; 98.0; 118.9; 122.8; 126.2; 127.4; 127.8; 128.0; 128.2; 128.5; 130.3; 130.9; 136.7; 146.0; 150.0; 152.9; 156.3; 156.7; 157.7; 174.0

EXAMPLE 7

7-[3-(4-tert-butoxycarbonyl)aminobutyl)-tert-butoxycarbonylamino-propoxyiminomethyl]-20S-camptothecin [ST2872].

N'',N'''-(ditert-butoxycarbonyl)-aminobutylaminoethoxyamine (NMR (CDCl$_3$): 4.65 (NHBoc), 3.9 (CH$_2$—O), 3.3-3.6 (Boc-N-CH$_2$ and —ONH$_2$), 3.05-3.25 (CH$_2$NHBoc and CH$_2$N-Boc), 1.45-1.55 (CH$_2$—CH$_2$), 1.45 (18 H, 2 Boc) (200 mg) was prepared from N-Boc-4-aminobutanol (500 mg), via mesylation followed by reaction with ethanolaminie, Boc protection of the free NH group, Mitsunobu reaction with N-hydroxyphthalimide, and hydrazinolysis.

7-Formylcamptothecin (55 mg, 0.145 mmol) was dissolved in 2 ml of ethanol, added with 100 mg of N'',N'''-(ditert-butoxycarbonyl)-aminobutylaminoethoxyamine in 1 ml of ethanol, and refluxed 8 hr. Evaporation and chromatography on silica gel with dichloromethane:MeOH (97:3) gave 51 mg (50%) of the title compound, mp 153° C., R$_f$ 0.2 in CH$_2$Cl$_2$:MeOH (97:3), NMR (DMSO-d$_6$): 9.4 (s, CH=), 8.85

$^1$H-NMR (300 MHz, CDCl$_3$, δ): 0.87 (t, H$_3$ -18E+H$_3$-18Z), 1.45-1.65 (m, BOC E+BOC Z+—CH$_2$CH$_2$-Z+CH$_2$CH$_2$-E), 1.87 (m, H$_2$-19E+H$_2$-19Z), 2-80-3.65 (m, 3 CH$_2$-N-Z+3 CH$_2$-N-E), 4.25-4.35 (m, CH$_2$—O-Z), 4.40-4.52 (m, CH$_2$—O-E), 4.60 (brs, NH), 5.10 (brs, -NH), 5.20-5.45 (m, H-17-Z+H-17-E+H-5-Z), 5.65-5.75 (m, H-5E), 7.65-7.75 (m, H-14-Z+H-14-E+2Ar Z), 7.75-7.85 (m, 2Ar-E), 7.90 (d, 1ArZ), 8.05 (s, —CH=N-Z), 8.25-8.35 (m, 2ArE+1Ar Z), 9.05 (s, —CH=N-E). E:Z ratio=55:45 (by NMR).

Cytotoxic activity on NCl—H460 cells

NCl—H460 non-microcytoma lung cancer cells were kept in RPMI 1640 culture medium containing 10% FCS and 1% glutamine. The cytotoxicity test to analyse the activity of the molecules was performed as follows. The cells were seeded in a volume of 250 µl in 96-well plates and incubated for 2 hours at 37° C. with scalar concentrations of the products in a humidified atmosphere containing 5% CO$_2$. At the end of the incubation, the molecules were removed by overturning the plates and adding sterile buffered saline solution (PBS) three times. The RPMI 1640 culture medium containing 10% FCS (200 µl) was added to the wells and the plates were incubated for another 72 hours. At the end of the incubation, the plates were overturned again and dried on paper, before adding 200 µl of PBS and 50 µl of 80% TCA. The plates were incubated again in ice for at least 1 hour. The TCA was removed by overturning the plates and the plates were first dried on paper and then washed three times by immersion in distilled water and overturning. The plates were dried first on paper and then in a thermostatically regulated incubator at 60° C. for 10 min. 200 µl of 0.4% sulforodamine B in 1% acetic acid were added to all wells. The plates were incubated at room temperature for another 30 min. The sulforodamine B was removed by overturning, the plates were washed by immersion in 1% acetic acid three times and then dried first on blotting paper and then in the thermostat at 60° C. for 10 min. Lastly, 200 µl of Tris base 10 mM were added to all wells and the plates were subjected to stirring for at least 20 min. The optical density was measured with a Multiskan spectrophotometer at 540 nm. Incubation with the products was capable of inhibiting proliferation in a concentration-dependent manner. Table 1 presents the IC$_{50}$ values (product concentration that inhibits cell survival by 50%]. ST2544 and ST2598 showed comparable, very potent cytotoxicity on the lung cancer line used.

The results are presented in the following table.

TABLE 1

Cytotoxicity of camptothecin derivatives

| Compound | IC$_{50}$ (nM ± SD) |
|---|---|
| ST2544 | 12.9 ± 1.8 |
| ST2598 | 15 ± 2 |
| ST2615 | >200 |
| ST2664 | >200 |
| ST2665 | >200 |
| ST2729 | 34 ± 7 |
| ST2872 | >200 |

Effect on *Saccharornzces cerevisiae* yeast model in vitro and in vivo

To identify camptothecin derivatives that overcome the resistance to camptothecin induced by point mutations on topisomerase I DNA in the *Saccharomyces cerevisiae* yeast model, an in-vivo and an in-vitro system were used in parallel.

For the in-vivo system, the yeast strain EKY3 (top1Δ) was transformed with YCpGAL1 plasmids as control and with different plasmids containing the mutants (YCpGAL1-hTOP1G363C, YCpGAL1-hTOP1K720E, YCpGAL-1hTOP1A653 P), which prove resistant to camptothecin. A number of mutations are present close to the active site of the enzyme (tyrosine 723) and others around position 363 which corresponds to a very well conserved region.

Before effecting the transformation of the yeasts, the yeasts were unfrozen and plated with a sterile bent glass rod in 90-mm plates containing sterile solid YPDa medium (10 g of yeast extract, 20 g of peptone, 20 g of dextrose, 0.7 g of adenine, 20 g of glucose, 20 g of agar per liter). Colonies formed after 48-72 hours in an incubator at 30° C.

One day before the transformation, a single yeast colony sample was taken with a sterile Gilson tip and inoculated in 5 ml of sterile liquid YPDA medium (the above-mentioned medium without agar). The colony was grown overnight under stirring at 30° C. On the day after, 5 ml of the saturated culture were diluted in sterile liquid YPDA medium and grown at 30° C. up to an optical density of 1.0 at 600 nm. The cells were centrifuged for 5 min at 4000× g, at room temperature and the precipitate was resuspended in 25 ml of a (T/E) solution containing Tris-EDTA (TE) 10 mM pH 7.5, EDTA 1 mM and lithium acetate 100 mM. The yeast suspension was centrifuged for 5 min at 4000× g at room temperature. The precipitate was resuspended in the same previous fresh solution (approximately 500 µl), so as to have 2×10$^9$ cells/ml. To accomplish the transformation, 200 µg of carrier DNA, 1 µg of plasmid DNA and 200 µl of competent cells were placed in an Eppendorf spectrophotometer. 1.2 ml of a TE/lithium acetate solution containing PEG 40% were added and the yeast suspension was stirred for 30 min at 30° C. A thermal shock was generated by placing the yeast suspension at 42° C. for 15 min and then plating it in selective plates, i.e. uracil-free plates containing complete minimal medium (CM) (1.3 g of dropout powder containing various amino acids but lacking uracil, 1.7 g of yeast nitrogen base without amino acids and ammonium sulphate, 5 g of ammonium sulphate, 20 g of glucose and 20 g of agar per liter). The plates were incubated at 30° C. until transformation.

Before treating the yeasts with the camptothecin derivatives (in-vivo spot test), the transformed colonies were inoculated with a Gilson tip in 5 ml sterile liquid CM medium. The colonies were grown overnight under stirring at 30° C. On the day after, the optical density of the colonies was measured at 600 nm and a dilution of the colonies was performed in order to obtain an optical density of 0.3. From this first dilution 10-fold serial dilutions were obtained (1:10, 1:100, 1:1000) in 96-well plates. Five μl of each dilution were pipetted onto 90-mm plates containing solid CM medium. For the controls 2% glucose and 2% galactose were added, whereas for the dilutions treated with the camptothecin derivatives 2% galactose and the products at the 45 μM concentration were added. The colonies were incubated at 30° C. for 48-72 hours and analysed macroscopically.

The effect of the camptothecin derivatives ST2544 and ST2598 was evaluated. Topoisomerase I wild-type DNA presented a phenotype of sensitivity to ST2544 and ST2598, whereas the mutated enzymes G363C and A653P proved resistant to the derivatives tested. The K720E mutant, however, presented a phenotype of sensitivity to the ST2544 derivative.

The results are presented in the following table.

TABLE 2

Growth of *Saccharomyces cerevisiae* yeast in the presence of camptothecin derivatives in vivo

| Drug | TOP1 | G363C | K720E | A653P |
|---|---|---|---|---|
| DMSO | ++++ | ++++ | ++++ | ++++ |
| ST2544 | ---- | ++++ | +--- | ++++ |
| ST2598 | ---- | ++++ | ++++ | ++++ |

From left to right each symbol denotes the growth of the 4 serial yeast dilutions.
+ Viability of *Saccharomyces cerevisiae* yeast;
− Lethality of *Saccharomyces cerevisiae* yeast.

Effect of ST2544 Against MKN-28 Human Gastric Carcinoma

Tumor fragments were inoculated on both flanks at day 0. Treatment started when tumors were just palpable. The molecule was given by oral route and intravenously according to the schedule q4d×4. During the treatment, animals were inspected every day for mortality. Physical appearance, behavior and general and local clinical signs of the mice will be observed daily. Any deviation from normality was recorded. All animals were weighed during the whole treatment period, in order to calculate the percent body weight loss due to the treatment.

Tumor volume inhibition % in treated over control tumors was evaluated 20 days after last treatment. To determine the antitumor activity of the drug, tumor diameters was measured biweekly with a Vernier caliper. The formula TV (mm$^3$)= [length (mm)×width (mm)$^2$]/2 was used, where the width and the length are the shortest and the longest diameters of each tumor, respectively.

When tumors reached a weight of about 2 g, the mice were sacrificed by cervical dislocation. LCK (log cell kill) as index of efficacy was calculated to evaluate the persistence of the effect of the molecule at the end of the treatment. The results are reported in table 3.

TABLE 3

Antitumor activity of ST2544 (q4d×4) p.o. or i.v. in athymic nude mice bearing s.c. the MKN-28 human gastric carcinoma

| Drug | Dose (mg/kg) | TVI % | LCK (1000 mm$^3$) | BWL % | Tox |
|---|---|---|---|---|---|
| ST2544 iv | 1 | 34 | 0.2 | 1 | 0/4 |
| iv | 2 | 36 | 0.2 | 6 | 0/4 |

TABLE 3-continued

Antitumor activity of ST2544 (q4d×4) p.o. or i.v. in athymic nude mice bearing s.c. the MKN-28 human gastric carcinoma

| Drug | Dose (mg/kg) | TVI % | LCK (1000 mm$^3$) | BWL % | Tox |
|---|---|---|---|---|---|
| iv | 4 | 66 | 0.8 | 0 | 0/4 |
| ST2544 p.o. | 1 | 28 | 0.1 | 5 | 0/4 |
| p.o. | 2 | 62 | 0.5 | 1 | 0/4 |
| p.o. | 4 | 72 | 1 | 7 | 0/4 |

When ST2544 was delivered by oral route showed to significantly inhibit the tumor growth at 4 and 2 mg/kg (q4d×4), since IVI was >50%, whereas when it was given intravenously was efficacious at 4 mg/kg (q4d×4) (TVI=66%). The persistence of the effect on tumor growth measured at the end of the treatment was observed after oral administration at 4 mg/kg (LCK=1).

The invention claimed is:
1. Compounds with general formula (I)

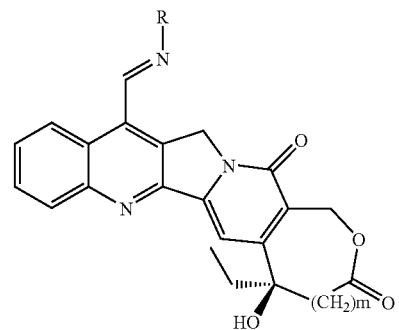

in which

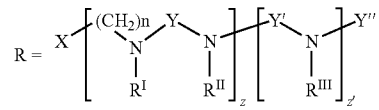

m is the number 0 or 1;
Z and Z' are an integer ranging from 0 to 2 when they are different or are an integer ranging from 1 to 2 when they are the same;
Y and Y', which can be the same or different, are (CH$_2$)$_{n1}$; (CH$_2$)$_{n2}$—CH[NR$^{VII}$(CH$_2$)$_{n4}$—NHR$^I$]—(CH$_2$)$_{n3}$; CH$_2$—CH[CH$_2$—CH$_2$]$_2$— or (CH$_2$)$_{n2}$—N[(CH$_2$)$_{n4}$—NHR$^{IV}$]—(CH$_2$)$_{n3}$;
Y" is selected from the group consisting of H; cycloalkyl C$_3$-C$_7$; (CH$_2$)$_{n5}$—N[CH$_2$—CH$_2$]$_2$N—(CH$_2$)$_{n6}$NHR$^V$; (CH$_2$)n$_7$ CH[CH$_2$—CH$_2$]$_2$NR$^V$;
X is O, or is a simple bond;
n-n7, which can be the same or different, are an integer ranging from 0 to 5;
R$^I$, R$^{II}$, R$^{III}$, R$^{IV}$, and R$^V$, which can be the same or different, are a protective group for the nitrogen to which they are bound, said protective group is selected from the group consisting of:
CO$_2$R$^{VI}$; CO$_2$CH$_2$Ar; CO$_2$-(9-fluorenylmethyl); (CH$_2$)$_{n5}$—NH CO$_2$R$^{VI}$; (CH$_2$)$_{n5}$—NHCO$_2$CH$_2$Ar; (CH$_2$)$_{n5}$—NHCO$_2$-(9-fluorenylmethyl);

$R^{VI}$ is a straight or branched $(C_1-C_6)$alkyl;

$R^{VII}$ is H or $R^I-R^V$;

Ar is a $C_6-C_{12}$ aromatic residue, such as phenyl, optionally substituted with one or more groups selected from: halogen, hydroxy, $C_1-C_5$ alkyl, $C_1-C_5$ alkoxy, phenyl, cyano, nitro, —$NR^{VIII}R^{IX}$, where $R^{VIII}$ and $R^{IX}$, which can be the same or different, are hydrogen, straight or branched $(C_1-C_5)$ alkyl, or Ar is a heterocyclic group, said heterocyclic group containing at least one heteroatom selected from a nitrogen atom, optionally substituted with a $(C_1-C_5)$ alkyl group, and/or oxygen and/or sulphur; said heterocycle can be substituted with one or more groups selected from halogen, hydroxy, $C_1-C_5$ alkyl, $C_1-C_5$ alkoxy, phenyl, cyano, nitro, —$NR^{VIII}R^{IX}$, where $R^{VIII}$ and $R^{IX}$, which can be the same or different, are hydrogen, straight or branched $(C_1-C_5)$ alkyl, the N1-oxides, racemic mixtures, their individual enantiomers, their individual diastereoisomers, the E and Z forms, their mixtures, and pharmaceutically acceptable salts.

2. A compound according to claim 1, in which the protective groups are selected from the group consisting of tert-butoxycarbonyl; benzyloxycarbonyl and 9-fluorenyl-methyloxycarbonyl.

3. A compound according to claim 1, in which m is 0.

4. A compound according to claim 3, selected from the group consisting of:

tert-butylester of 20S-(4-{[3-(7-camptothecinylidene-amino)-propyl]-tert-butoxycarbonyl-amino}-butyl)-(3-tert-butoxycarbonylaminopropyl)-carbamic acid;

tert-butylester of 20S-(4-{[3-(7-camptothecinylidene-amino)-propyl]-tertbutoxycarbonyl-amino}-butyl)-carbamic acid; and benzyl ester of 20S-(4-{[3-(7-camptothecinylidene-amino)-propyl]-benzyloxycarbonyl-amino}-butyl)-carbamic acid.

5. A compound according to claim 1, in which m is 1.

6. A compound according to claim 5, selected from the group consisting of:

tert-butylester of 20RS-(4-{[3-(7-homocamptothecinylidene-amino)-propyl]-tertbutoxycarbonyl-amino}-butyl)-(3-tert-butoxycarbonylaminopropyl)-carbamic acid;

tert-butyl ester of 20RS-(4-{[3-(7-homocampto-thecinylidene-amino)-propyl]-tertbutoxycarbonyl-amino}-butyl)-carbamic acid; and benzyl ester of 20S-(4-{[3-(7-homocamptothecinylidene-amino)-propyl]-benzyloxycarbonyl-amino}-butyl)-carbamic acid.

7. A pharmaceutical composition containing at least one compound according to claim 1 as the active ingredient in admixture with at least one pharmaceutically acceptable vehicle and/or excipient.

8. A method of inhibiting topoisomerase comprising administering to a subject in the need of the same an effective amount of a compound of claim 1.

9. A method of treating cancer, wherein said cancer is non-microcytoma lung cancer or gastric cancer comprising administering to a subject in the need of the same an effective amount of a compound of claim 1.

* * * * *